(12) United States Patent
Okano

(10) Patent No.: US 8,758,797 B2
(45) Date of Patent: *Jun. 24, 2014

(54) PVA AND SILICA PARTICLE BLOOD VESSEL MODEL

(75) Inventor: Yoshio Okano, Ootsu (JP)

(73) Assignee: Yuugengaisha Seiwadental, Ootsu-shi (JP)

( * ) Notice: Subject to any disclaimer, the term of this patent is extended or adjusted under 35 U.S.C. 154(b) by 148 days.

This patent is subject to a terminal disclaimer.

(21) Appl. No.: 13/392,177

(22) PCT Filed: Sep. 9, 2010

(86) PCT No.: PCT/JP2010/065473
§ 371 (c)(1),
(2), (4) Date: Feb. 24, 2012

(87) PCT Pub. No.: WO2011/040200
PCT Pub. Date: Apr. 7, 2011

(65) Prior Publication Data
US 2012/0156666 A1 Jun. 21, 2012

(30) Foreign Application Priority Data

Sep. 30, 2009 (JP) ................................. 2009-228296
Sep. 30, 2009 (JP) ................................. 2009-228305

(51) Int. Cl.
*A61F 2/02* (2006.01)
*G09B 23/28* (2006.01)
(52) U.S. Cl.
CPC .................................. *G09B 23/285* (2013.01)
USPC ....................................................... 424/425
(58) Field of Classification Search
CPC ......................... A61L 27/3625; A61L 27/3679
See application file for complete search history.

(56) References Cited

U.S. PATENT DOCUMENTS 3,592,936 A 7/1971 Marcu et al.
3,738,957 A * 6/1973 Iier ................................ 524/557

(Continued)

FOREIGN PATENT DOCUMENTS

EP 0135628 A2 4/1985
JP 2-026567 A 1/1990

(Continued)

OTHER PUBLICATIONS

International Search Report of PCT/JP2010/065473, mailing date Oct. 5, 2010.

(Continued)

*Primary Examiner* — Carlos Azpuru
(74) *Attorney, Agent, or Firm* — Westerman, Hattori, Daniels & Adrian, LLP

(57) ABSTRACT

A blood vessel model which imitates a human blood vessel including an aqueous gel made from polyvinyl alcohol having an average polymerization degree of 300 to 3500 and a saponification degree of 90% by mole or more, and silica particles; and a method for producing a blood vessel model which imitates a human blood vessel, including filling a mixed solution containing polyvinyl alcohol having an average polymerization degree of 300 to 3500 and a saponification degree of 90% by mole or more, silica particles and water in a mold for forming a blood vessel model, and freezing the mixture at a temperature of −10° C. or lower, followed by thawing. The blood vessel model can be suitably used as a blood vessel model for practicing insertion of a stent graft into an aneurysm, a blood vessel model for practicing resection or ligation surgery of a blood vessel, and the like.

8 Claims, 5 Drawing Sheets

(56) References Cited

U.S. PATENT DOCUMENTS

| | | |
|---|---|---|
| 5,266,224 A | 11/1993 | Sharif |
| 5,349,008 A | 9/1994 | Takada et al. |
| 5,977,021 A | 11/1999 | Aoyama et al. |
| 7,521,434 B2 | 4/2009 | Leshchiner et al. |
| 7,993,140 B2 | 8/2011 | Sakezles |
| 2008/0260831 A1 | 10/2008 | Badylak et al. |
| 2009/0068627 A1 | 3/2009 | Toly |
| 2010/0175845 A1 | 7/2010 | Gauto et al. |

FOREIGN PATENT DOCUMENTS

| | | |
|---|---|---|
| JP | 02-026567 A | 1/1990 |
| JP | 04-062010 A | 2/1992 |
| JP | 05-027776 U | 4/1993 |
| JP | 06-004768 U | 1/1994 |
| JP | 06-226748 A | 8/1994 |
| JP | 11-167342 A | 6/1999 |
| JP | 2000-080126 A | 3/2000 |
| JP | 2005-195696 A | 7/2005 |
| JP | 2006-126686 A | 5/2006 |
| JP | 2007-316343 A | 12/2007 |
| JP | 2007-316434 A | 12/2007 |
| JP | 2007316434 | * 12/2007 |
| JP | 2008-241988 A | 10/2008 |
| JP | 2008-261990 A | 10/2008 |

OTHER PUBLICATIONS

International Search Report of PCT/JP2010/057411, mailing date Jul. 13, 2010.

Lee, et al., "An In situ Injectable Physically and Chemically Gelling NIPAAm-based Copolymer System for Embolization" NIH Public Access, dated Jun. 2006.

Peppas, et al., "Mechanistic analysis of protein delivery from porous poly(vinyl alcohol) systems", J. Drug Sci. Tech. vol. 14, No. 4, pp. 285-284, 2004.

Nittke, et al., "Thermodynamic properties of small amorphous and crystalline Silica particles at low temperatures", European Physics Journal, vol. 8, pp. 19-30, 1999.

European Search Report Application No. 10820320.9, Dated Apr. 3, 2013 (4 pp).

U.S. Office Action dated Apr. 16, 2103, issued in related U.S. Appl. No. 13/266,622 (25 pp).

U.S. Office Action dated Oct. 25, 2013, issued in related U.S. Appl. No. 13/266,622 (22 pp).

* cited by examiner

[FIG.1]
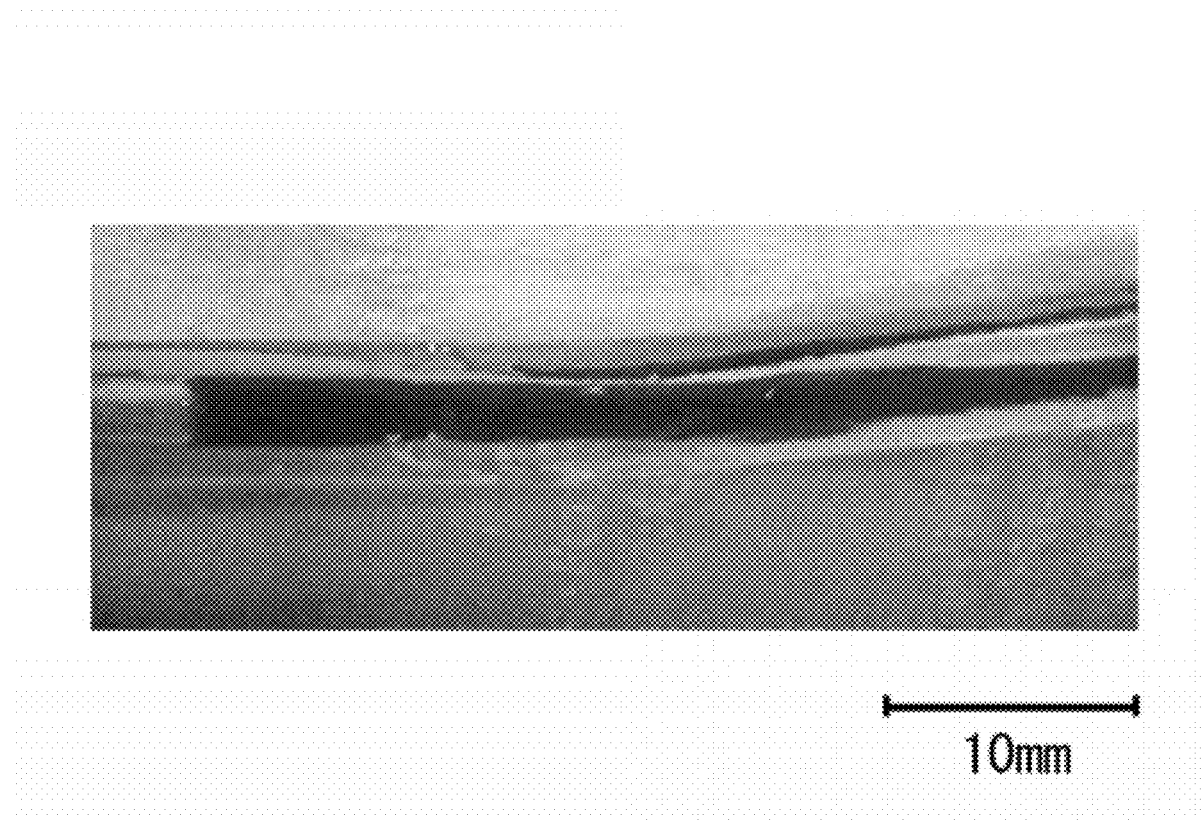

[FIG.2]
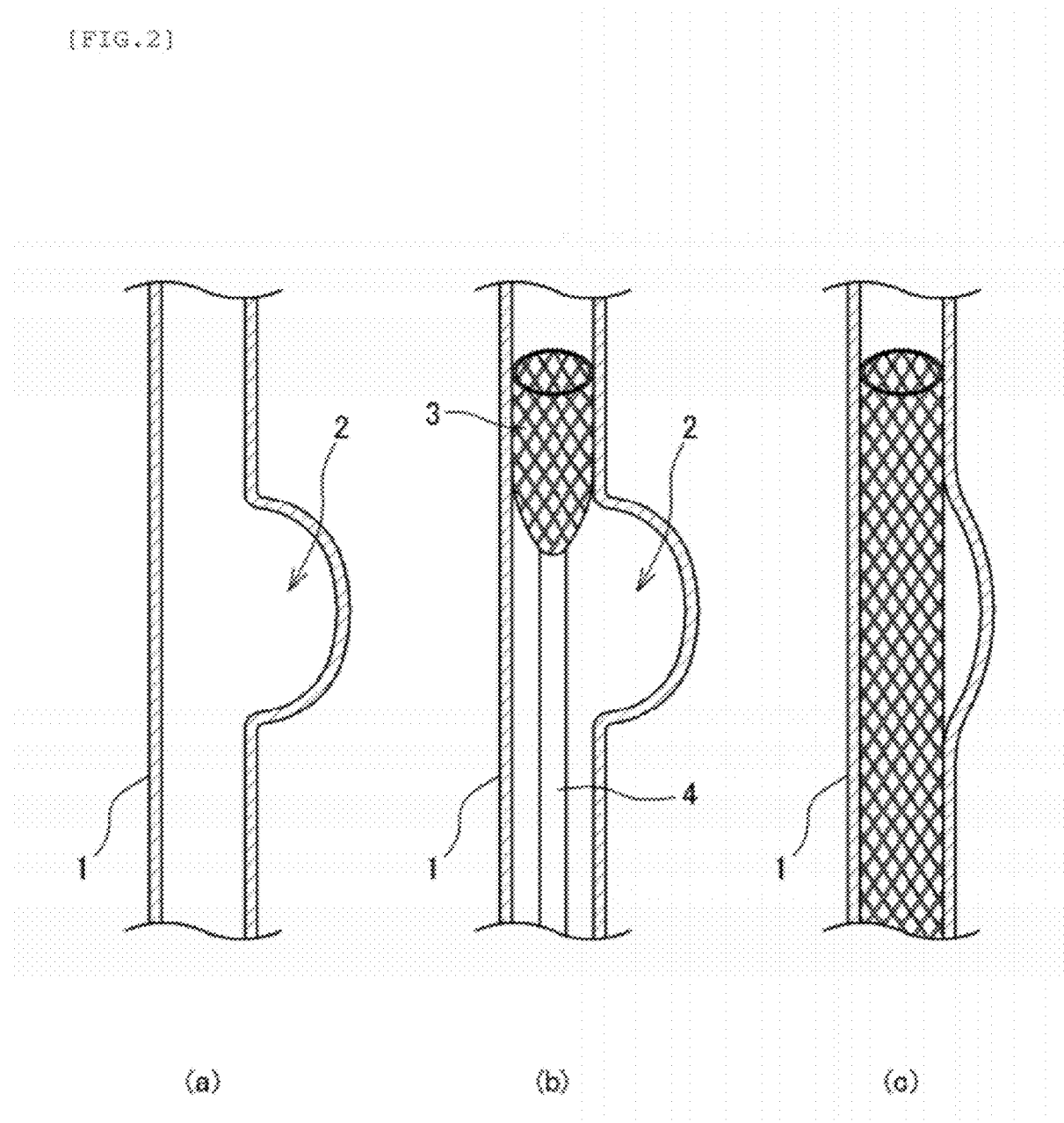

[FIG.3]
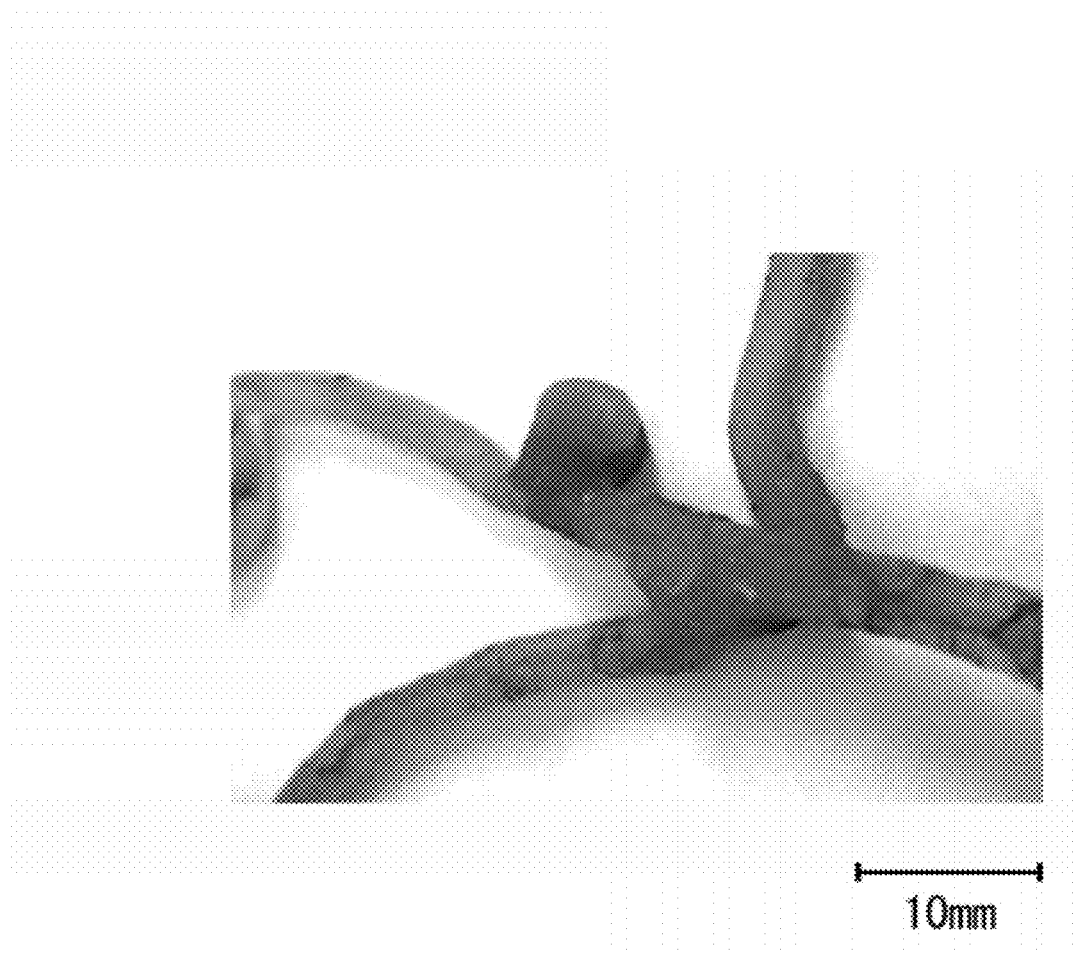

[FIG.4]
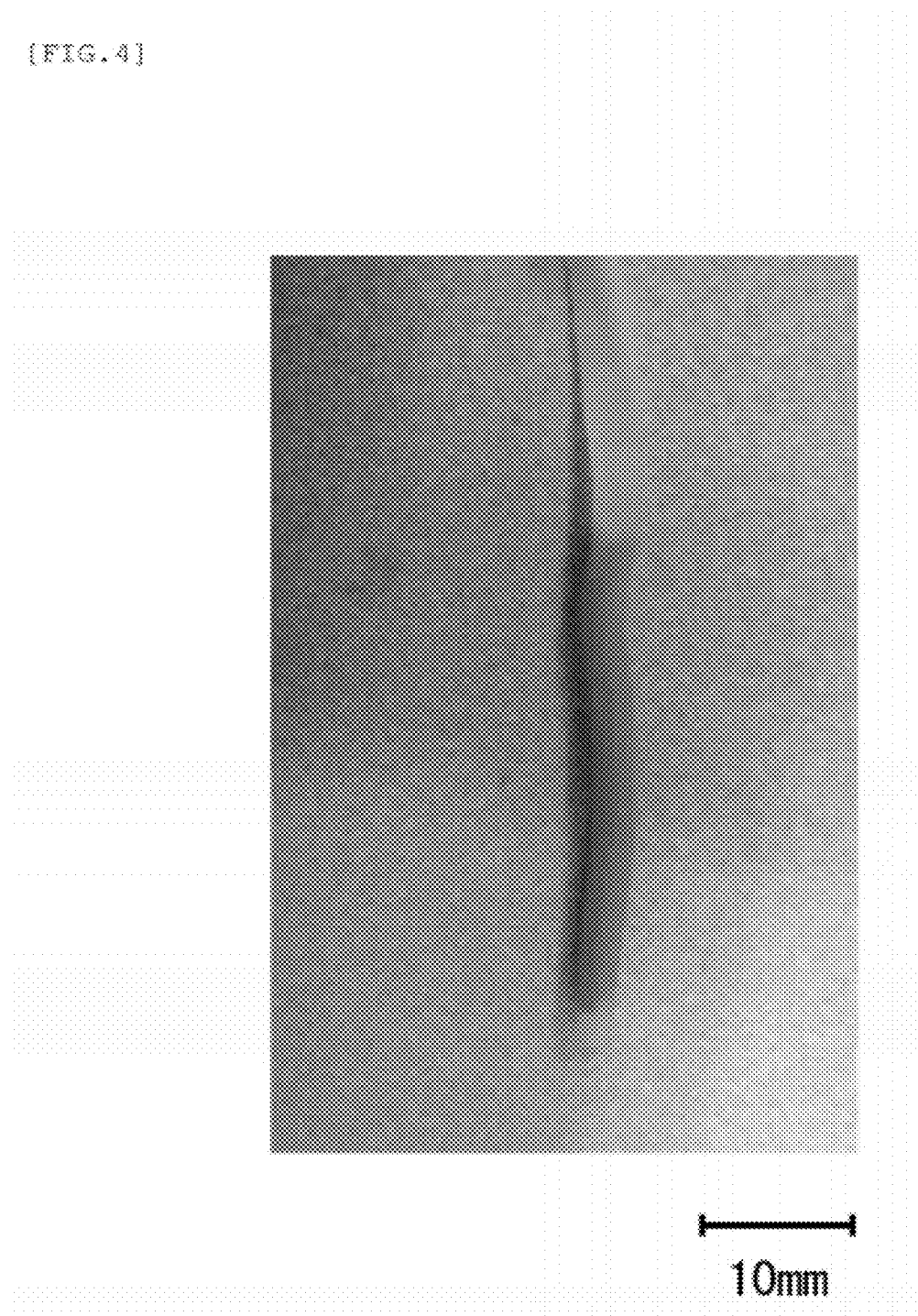
10mm

[FIG.5]
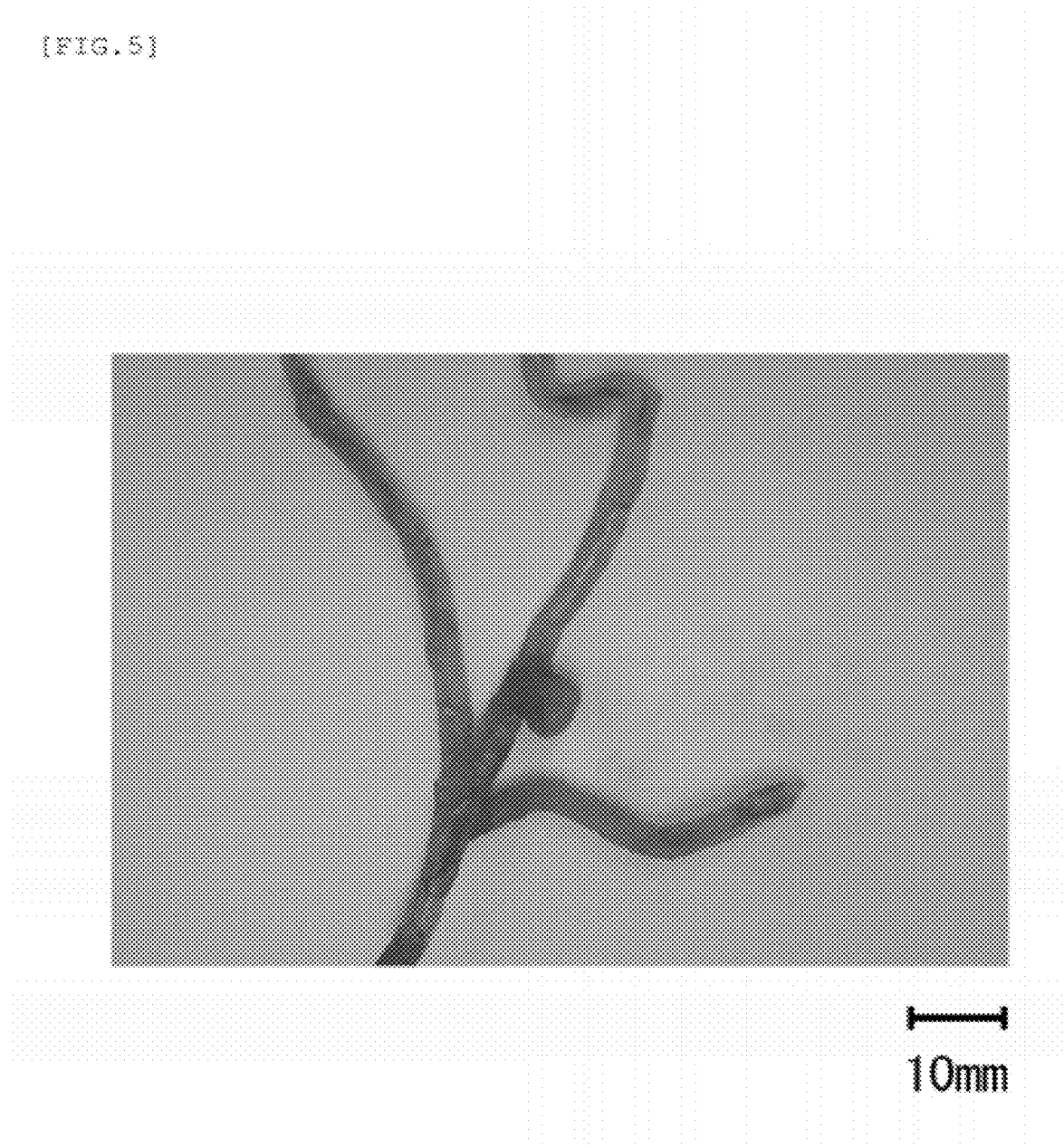

PVA AND SILICA PARTICLE BLOOD VESSEL MODEL

TECHNICAL FIELD

The present invention relates to a blood vessel model. More particularly, the present invention relates to a blood vessel model which imitates a human blood vessel, and which can be suitably used, for example, as a blood vessel model for practicing insertion of a stent graft into an aneurysm, a blood vessel model for practicing resection or ligation surgery of a blood vessel, and the like.

BACKGROUND ART

Among surgeries carried out by surgeons, insertion of a stent graft into an aneurysm and resection or ligation surgery of a blood vessel require careful and skilled techniques, which spell the difference between life and death. Therefore, it is necessary for medical interns and medical students as well as vascular surgeons to repeatedly carry out surgical training by using a blood vessel model so as to learn skilled techniques.

There have hitherto been proposed, as a material which constitutes a blood vessel model for practicing surgery, a synthetic rubber, a diene-based rubber, and the like (see, for example, paragraph [0009] in Patent Literature 1 and paragraph [0015] in Patent Literature 2); a natural rubber, a silicone rubber, an acrylic rubber, an olefinic rubber, polyurethane, and the like (see, for example, paragraph [0006] in Patent Literature 3, paragraph in Patent Literature 4, paragraph [0015] in Patent Literature 5 and paragraph [0013] in Patent Literature 6); polyvinyl chloride, polybutadiene, ionomer, low density polyethylene, and the like (see, for example, paragraph [0017] in Patent Literature 7); and the like. A tube made of a silicone rubber has been widely used among these materials, since the silicone rubber is comparatively similar to a blood vessel of the human body. However, since the above-mentioned materials such as the silicone rubber have very strong water repellency, the materials have neither hydrophilicity nor flexibility like the blood vessel of the human body. Therefore, it cannot be said that the blood vessel model made of the material is suited for vascular surgeons to perform manipulation training.

Accordingly, it has recently been required by researchers of medical colleges, surgical hospitals and the like, including vascular surgeons, to develop a blood vessel model which can be suitably used as a blood vessel model for practicing resection or ligation surgery of a blood vessel, a blood vessel model for practicing insertion of a stent graft into an aneurysm, and the like.

PRIOR ART DOCUMENTS

Patent Literatures

Patent Literature 1: Japanese utility model publication No. Hei 05-0027776
Patent Literature 2: Japanese patent publication No. 2005-195696
Patent Literature 3: Japanese utility model publication No. Hei 06-0004768
Patent Literature 4: Japanese patent publication No. Hei 11-0167342
Patent Literature 5: Japanese patent publication No. 2007-316343
Patent Literature 6: Japanese patent publication No. 2008-261990
Patent Literature 7: Japanese patent publication No. 2006-126686

SUMMARY OF THE INVENTION

Problems to be Solved by the Invention

An object of the present invention is to provide a blood vessel model which has moderate hydrophilicity, flexibility (resilience) and a surface free from stickiness, and which can be suitably used as a blood vessel model for practicing insertion of a stent graft into an aneurysm, a blood vessel model for practicing resection or ligation surgery of a blood vessel, and the like.

Means for Solving the Problems

The present invention relates to
(1) a blood vessel model which imitates a human blood vessel, including an aqueous gel made from polyvinyl alcohol having an average polymerization degree of 300 to 3500 and a saponification degree of 90% by mole or more, and silica particles;
(2) the blood vessel model according to the above (1), wherein colloidal silica is used as the silica particles;
(3) the blood vessel model according to the above (1) or (2), wherein the amount of the silica particles is from 0.01 to 50 parts by weight based on 100 parts by weight of the polyvinyl alcohol;
(4) the blood vessel model according to any one of the above (1) to (3), wherein the blood vessel model is produced by freezing a mixed solution containing the polyvinyl alcohol, the silica particles and water at a temperature of −10° C. or lower, followed by thawing;
(5) the blood vessel model according to the above (1), wherein the aqueous gel is a cross-linked gel;
(6) the blood vessel model according to the above (5), wherein the cross-linked gel is a cross-linked gel being cross-linked with dimethyl sulfoxide;
(7) the blood vessel model according to the above (6), wherein the blood vessel model is produced by cooling a mixed solution containing polyvinyl alcohol, silica particles, dimethyl sulfoxide and water to a temperature of −10° C. or lower, followed by thawing;
(8) a method for producing a blood vessel model which imitates a human blood vessel, which includes filling a mixed solution containing polyvinyl alcohol having an average polymerization degree of 300 to 3500 and a saponification degree of 90% by mole or more, silica particles and water in a mold for forming a blood vessel model, and freezing the mixture at a temperature of −10° C. or lower, followed by thawing;
(9) the method for producing a blood vessel model according to the above (8), wherein colloidal silica is used as the silica particles;
(10) the method for producing a blood vessel model according to the above (8) or (9), wherein the amount of the silica particles is from 0.01 to 50 parts by weight based on 100 parts by weight of the polyvinyl alcohol;
(11) the method for producing a blood vessel model according to any one of the above (8) to (10), wherein the concentration of the polyvinyl alcohol in the mixed solution is from 1 to 40% by weight;

(12) the method for producing a blood vessel model according to any one of the above (8) to (11), wherein the temperature of the blood vessel model formed after thawing is controlled to 35° to 80° C.;

(13) the method for producing a blood vessel model according to any one of the above (8) to (12), wherein the mixed solution further contains dimethyl sulfoxide; and

(14) the method for producing a blood vessel model according to the above (13), wherein the ratio of the dimethyl sulfoxide to water (dimethyl sulfoxide/water:volume ratio) is from 50/50 to 95/5.

Effects of the Invention

The blood vessel model of the present invention has moderate hydrophilicity and flexibility (resilience), and has a surface free from stickiness. Therefore, the blood vessel model can be suitably used as a blood vessel model for practicing insertion of a stent graft into an aneurysm, a blood vessel model for practicing resection or ligation surgery of a blood vessel, and the like.

BRIEF DESCRIPTION OF THE DRAWINGS

[FIG. 1] A photograph, which is substituted for a drawing, of a blood vessel model obtained in Example 1 of the present invention.

[FIG. 2 a,b, and c] A schematic drawings for the explanation of manipulation training carried out by inserting a stent graft into the blood vessel model having a large aneurysm of the present invention.

[FIG. 3] A photograph, which is substituted for a drawing, of a blood vessel model obtained in Example 6 of the present invention.

[FIG. 4] A photograph, which is substituted for a drawing, of a blood vessel model obtained in Example 7 of the present invention.

[FIG. 5] A photograph, which is substituted for a drawing, of a blood vessel model obtained in Example 14 of the present invention.

DETAILED DESCRIPTION OF THE INVENTION

The blood vessel model of the present invention is a blood vessel model which imitates a human blood vessel. The blood vessel model is characterized in that the blood vessel model contains an aqueous gel made from polyvinyl alcohol having an average polymerization degree of 300 to 3500 and a saponification degree of 90% by mole or more, and silica particles.

The blood vessel model of the present invention can be easily produced, for example, by freezing a mixed solution containing polyvinyl alcohol having an average polymerization degree of 300 to 3500 and a saponification degree of 90% by mole or more, water and silica particles at a temperature of −10° C. or lower, followed by thawing.

The average polymerization degree of the polyvinyl alcohol as determined by a viscosity method is preferably 300 or more, more preferably 500 or more, and still more preferably 1000 or more from the viewpoint of increase in mechanical strength such as tensile strength of the blood vessel model of the present invention, and preferably 3500 or less, more preferably 3000 or less, and still more preferably 2500 or less from the viewpoint of imparting of moderate flexibility (resilience).

The saponification degree of the polyvinyl alcohol is preferably 90% by mole or more, more preferably 95% by mole or more, and still more preferably 98% by mole or more from the viewpoint of increase in mechanical strength such as tensile strength and flexibility (resilience) of the blood vessel model of the present invention. There is no limitation in the upper limit of the saponification degree of the polyvinyl alcohol. It is preferred that the higher the saponification degree of the polyvinyl alcohol is, and it is more preferable that the polyvinyl alcohol is a completely saponified polyvinyl alcohol.

The polyvinyl alcohol can be usually used in the form of an aqueous solution. When the polyvinyl alcohol is dissolved in water, the polyvinyl alcohol or water is preferably warmed in advance from the viewpoint of increase in solubility of the polyvinyl alcohol. The concentration of the polyvinyl alcohol in the aqueous solution of the polyvinyl alcohol is preferably 1% by weight or more, more preferably 3% by weight or more, and still more preferably 5% by weight or more from the viewpoint of increase in mechanical strength of the blood vessel model of the present invention, and the concentration of the polyvinyl alcohol is preferably 40% by weight or less, more preferably 30% by weight or less, and still more preferably 20% by weight or less from the viewpoint of improvement in moldability as well as sufficient dissolution of the wing polyvinyl alcohol in water.

The blood vessel model of the present invention has one of great features in that the blood vessel model contains silica particles. Since the blood vessel model of the present invention contains silica particles, the blood vessel model has a surface free from stickiness, and also has moderate hydrophilicity and flexibility (resilience). Therefore, the blood vessel model of the present invention can be suitably used as a blood vessel model for practicing insertion of a stent graft into an aneurysm, a blood vessel model for practicing resection or ligation surgery of a blood vessel, and the like.

In the present invention, the silica particles and the polyvinyl alcohol are used in combination as raw materials. Therefore, it is possible to efficiently obtain a blood vessel model which has a surface free from stickiness, also has moderate hydrophilicity and flexibility (resilience), and is excellent in mechanical strength such as tensile strength, by performing freezing and thawing of a mixed solution containing the silica particles and the polyvinyl alcohol only once without the repetition of an operation of freezing and thawing of the polyvinyl alcohol solution plural times, like in a conventional method.

The particle diameter of the silica particles is preferably from 3 to 100 nm or so from the viewpoint of enhancement in dispersion stability of the silica particles in the polyvinyl alcohol and smoothness of the blood vessel model of the present invention.

The amount of the silica particles is preferably 0.01 parts by weight or more, more preferably 0.05 parts by weight or more, and still more preferably 0.1 parts by weight or more based on 100 parts by weight of the polyvinyl alcohol from the viewpoint of increase in mechanical strength and flexibility (resilience) of the blood vessel model of the present invention, and preferably 50 parts by weight or less, more preferably 30 parts by weight or less, and still more preferably 20 parts by weight or less from the viewpoint of preventing the blood vessel model of the present invention from becoming hard. The silica particles can be usually mixed with the polyvinyl alcohol or its aqueous solution.

In the present invention, it is preferred that the silica particles are used in the form of colloidal silica. When the colloidal silica is used as the silica particles, it is possible to obtain a blood vessel model which has a surface free from stickiness and has moderate hydrophilicity and flexibility (resilience), and which can be suitably used as a blood vessel model for practicing insertion of a stent graft into an aneurysm, a blood vessel model for practicing resection or ligation surgery of a blood vessel, and the like.

The content of the silica particles in the colloidal silica is preferably from 3 to 40% by weight or so from the viewpoint of improvement in dispersion stability of the silica particles in the colloidal silica. The colloidal silica is commercially available, for example, from Nissan Chemical Industries, Ltd. under the trade name of SNOWTEX (registered trademark), and the like.

It is preferred that the aqueous gel is a cross-linked gel from the viewpoint of obtaining a blood vessel model of the present invention, which has moderate hydrophilicity, flexibility (resilience) and a surface free from stickiness, and which also has a large tensile strength.

It is preferred that the cross-linked gel is a cross-linked gel being cross-linked with dimethyl sulfoxide from the viewpoint of producing a blood vessel model having moderate hydrophilicity, flexibility (resilience) and a surface free from stickiness, and also having a large tensile strength.

The blood vessel model containing the cross-linked gel and the silica particles of the present invention can be easily produced, for example, by cooling a mixed solution containing polyvinyl alcohol having an average polymerization degree of 300 to 3500 and a saponification degree of 90% by mole or more, silica particles, dimethyl sulfoxide and water to a temperature of $-10°$ C. or lower, followed by thawing.

The polyvinyl alcohol can be added to a mixed solvent of dimethyl sulfoxide and water, water used in the mixed solvent, or a mixture prepared by adding the silica particles to the mixed solvent. It is preferred that the mixed solvent, water to be used in the mixed solvent, or the mixed solution is heated prior to the addition of the polyvinyl alcohol from the viewpoint of increase in solubility of the polyvinyl alcohol. There is no particular limitation in heating temperature in case of heating, and usually, it is preferred that the heating temperature is from $60°$ to $95°$ C. or so.

In the blood vessel model containing the cross-linked gel and the silica particles of the present invention, the content of the polyvinyl alcohol in the mixed solution containing the polyvinyl alcohol, the silica particles, dimethyl sulfoxide and water is preferably 1% by weight or more, more preferably 3% by weight or more, and still more preferably 5% by weight or more from the viewpoint of increase in mechanical strength such as tensile strength of the blood vessel model of the present invention, and the content of the polyvinyl alcohol is preferably 40% by weight or less, more preferably 30% by weight or less, and still more preferably 20% by weight or less from the viewpoint of increase in solubility of the polyvinyl alcohol and prevention of stickiness.

The ratio of dimethyl sulfoxide to water (dimethyl sulfoxide/water:volume ratio) is preferably 50/50 or more, more preferably 60/40 or more, and still more preferably 70/30 or more from the viewpoint of increase in mechanical strength such as tensile strength of the blood vessel model of the present invention, and the ratio is preferably 95/5 or less, more preferably 90/10 or less, and still more preferably 85/15 or less from the viewpoint of suppression of stickiness of the surface, and enhancement of flexibility (resilience) and hydrophilicity of the blood vessel model of the present invention.

In the blood vessel model containing the cross-linked gel and the silica particles of the present invention, the amount of the silica particles is preferably 0.01 parts by weight or more, more preferably 0.05 parts by weight or more, and still more preferably 0.1 parts by weight or more based on 100 parts by weight of water from the viewpoint of increase in mechanical strength such as tensile strength, prevention of stickiness and imparting moderate hydrophilicity of the blood vessel model of the present invention, and the amount of the silica particles is preferably 50 parts by weight or less, more preferably 30 parts by weight or less, and still more preferably 20 parts by weight or less from the viewpoint of enhancement in flexibility (resilience) of the blood vessel model of the present invention. When the silica particles are used in the form of colloidal silica, the amount of the above-mentioned water includes the amount of the water contained in the colloidal silica.

In the blood vessel model containing the cross-linked gel and the silica particles of the present invention, a mixed solution containing the polyvinyl alcohol, the silica particles, dimethyl sulfoxide and water is cooled to a desired temperature for a desired period of time to frozen the mixed solution. When the mixed solution is frozen, the mixed solution is gelled by cross-linking, and thereby a molded product containing a cross-linked gel and the silica particles is formed.

It is preferred that polysaccharide is added to the polyvinyl alcohol from the viewpoint of preventing the surface layer of a molded product from drying. It is preferred that the polysaccharide is added to the mixed solution from the viewpoint of increase in dispersion stability.

The polysaccharide includes, for example, chitin, deacetylated chitin, chitosan, chitosan acetate, chitosan maleate, chitosan glyconate, chitosan sorbate, chitosan formate, chitosan salicylate, chitosan propionate, chitosan lactate, chitosan itaconate, chitosan niacinate, chitosan gallate, chitosan glutamate, carboxymethyl chitosan, alkyl cellulose, nitrocellulose, hydroxypropyl cellulose, starch, collagen, alginate, hyaluronic acid, heparin, and the like. However, the present invention is not limited only to those exemplified ones. Among these polysaccharides, chitosan and its derivative are preferable, and chitosan is more preferable from the viewpoint of preventing the blood vessel model of the present invention from drying.

The chitosan includes, for example, those obtained by deacetylating chitin derived from crustaceans such as prawn, crab and cuttlefish. The chitosan is commercially easily available. The chitosan can be usually used in the form of powder. The molecular weight of the chitosan is not particularly limited, and is usually preferably from 10000 to 200000, and more preferably from 10000 to 40000.

The amount of the polysaccharide cannot be absolutely determined because the amount varies depending on its kind, and the amount is usually preferably 0.3 parts by weight or more, more preferably 0.5 parts by weight or more, and still more preferably 1 part by weight or more based on 100 parts by weight of the polyvinyl alcohol from the viewpoint of preventing the blood vessel model of the present invention from drying, and the amount is preferably 300 parts by weight or less, more preferably 250 parts by weight or less, and still more preferably 200 parts by weight or less from the viewpoint of imparting moderate resilience to the blood vessel model of the present invention.

It is preferred that polysaccharide is usually used in the form of aqueous solution from the viewpoint of enhancement in dispersion stability. The aqueous solution of the polysaccharide can be obtained, for example, by dissolving the polysaccharide in an aqueous solution of an acid such as acetic acid, hydrochloric acid or lactic acid so as to have a concentration of 0.5 to 10% by weight or so. The aqueous solution of the polysaccharide can be controlled to neutral to basic with a basic substance such as sodium hydroxide or potassium hydroxide as occasion demands.

The mixed solution may contain an additive, for example, a colorant such as a pigment or a dye, a perfume, an antioxidant, a mildewproofing agent or an antibacterial agent in a proper amount, so long as an object of the present invention is not hindered. It is preferred that these additives are usually added to the mixed solution from the viewpoint of improvement in dispersion stability. In order to make the blood vessel model of the present invention similar to a blood vessel of the human body, it is preferred to tint the mixed solution to the color similar to a blood vessel of the human body with a colorant.

The blood vessel model of the present invention can be produced by filling a mixed solution containing the polyvinyl alcohol, water, the silica particles and dimethyl sulfoxide as occasion demands into a mold for forming a blood vessel model, and freezing the mixed solution at a temperature of $-10°$ C. or lower, followed by thawing.

More specifically, the blood vessel model of the present invention can be produced, for example, by filling the mixed solution into a tube having an inner diameter corresponding to the diameter of a blood vessel of the human body; freezing the mixed solution at a temperature of $-10°$ C. or lower; thawing the frozen mixed solution; inserting a striped body having a diameter corresponding to the inner diameter of the blood vessel, such as a galvanized steel wire, a wire or a metal wire into the central portion of a molded product formed in the tube to form a passage of blood; and removing the tube and the striped body from the molded product. When the striped body is inserted into the central portion of the molded product, the molded product may be taken out from the interior of the tube through suction or extruding, followed by insertion of a striped body into the central portion of the molded product to form a passage of blood.

The tube includes, for example, a rubber tube made of a silicone rubber, a tube made of an elastomer, a resin tube made of a resin such as polypropylene, an acrylic resin or polycarbonate, and the like. However, the present invention is not limited only to those exemplified ones.

In the present invention, the blood vessel model can be produced, for example, by filling a mixed solution into a straight tube having an inner diameter corresponding to the external form of a blood vessel; inserting a core material having a diameter corresponding to the inner diameter of the blood vessel into the central portion of the straight tube; freezing the mixed solution at a temperature of $-10°$ C. or lower; thawing the frozen mixed solution; and removing the straight tube and the core material from the molded product.

The straight tube includes, for example, a resin tube made of a synthetic resin such as polypropylene, hard polyethylene, hard polyvinyl chloride, an acrylic resin, a polyester or polycarbonate, a glass tube, and the like. However, the present invention is not limited only to those exemplified ones. It is preferred that the inner diameter of the straight tube is determined in accordance with the diameter of a blood vessel of the living body.

The core material to be inserted into the straight tube includes, for example, a core material made of a synthetic resin such as polypropylene, hard polyethylene, hard vinyl chloride, an acrylic resin, a polyester or polycarbonate, a core material made of glass, a core material made of a metal, and the like. However, the present invention is not limited only to those exemplified ones.

In order to allow the core material inserted into the straight tube to be located at the central portion of the straight tube, it is preferred, for example, that an opening at one end of the straight tube is sealed with a shield plug having a through hole for inserting a core material into the central portion of the straight tube, and the core material is inserted into the through hole. In this case, the opening at one end of the straight tube may be sealed with the shield plug after inserting the core material into the through hole of the shield plug. The shield plug includes, for example, a rubber plug made of a rubber such as silicone rubber or natural rubber, a cork plug, and the like. However, the present invention is not limited only to those exemplified ones.

In the straight tube of which opening at one end is sealed with the shield plug and into which the core material is inserted, it is preferred that a mixed solution is poured in the gap between the straight tube and the core material, and then an opening at another end of the straight tube is sealed with a shield plug having a through hole for inserting the core material into the central portion in the same manner as described above. Next, the core material is inserted into the straight tube at the central portion. The mixed solution is poured to the inside of the strait tube, and thereafter the straight tube is sealed with a shield plug at both ends. The straight tube is frozen at a temperature of $-10°$ C. or lower so as to gel the mixed solution.

The freezing temperature of the mixed solution is preferably $-10°$ C. or lower, more preferably $-15°$ C. or lower, and still more preferably $-20°$ C. or lower from the viewpoint of increase in mechanical strength of the blood vessel model of the present invention, and the freezing temperature is preferably $-35°$ C. or higher, and more preferably $-30°$ C. or higher from the viewpoint of enhancement in productive efficiency of the blood vessel model of the present invention.

The period of time for cooling the mixed solution to the above-mentioned temperature is preferably from 1 to 10 hours or so, and more preferably from 3 to 8 hours or so from the viewpoint of increase in mechanical strength of the blood vessel model of the present invention and enhancement in productive efficiency.

The mixed solution is frozen by cooling to a desired temperature for a desired period of time. In this case, since the mixed solution is gelled, a molded product containing the aqueous gel and the silica particles is formed.

Next, the molded product is thawed. The molded product may be naturally thawed, for example, by allowing the molded product to stand at room temperature, or may be thawed by heating. From the viewpoint of increase in energy efficiency, natural thawing is preferable. The temperature at which the molded product is thawed is not particularly limited, and can be usually from room temperature to $40°$ C. or so, and preferably from $10°$ to $40°$ C. or so.

The blood vessel model of the present invention can be obtained by thawing the molded product in the above manner. The obtained blood vessel model can be used as it is without drying. The blood vessel model may be dried as occasion demands so as to make the blood vessel model similar to the blood vessel of the living body. The degree of drying cannot be absolutely determined since the degree varies depending on the kind of the blood vessel of the living body. Therefore, it is preferred that the degree of drying is appropriately controlled in accordance with the kind of the blood vessel. When the blood vessel model is dried by heating, the texture of the aqueous gel constituting the blood vessel model can be homogenized.

For example, when the blood vessel model is dried by heating, the blood vessel model can be dried in a drying chamber. When the blood vessel model is dried, the temperature of the blood vessel model is preferably $35°$ C. or higher, and more preferably $40°$ C. or higher from the viewpoint of homogenizing the texture of the aqueous gel, and the temperature is preferably $80°$ C. or lower, and more preferably $75°$ C. or lower from the viewpoint of improvement in gel elasticity and flexibility (resilience) of the blood vessel model. The period of time necessary for controlling the temperature of the blood vessel model to the above temperature cannot be absolutely determined, because the period of time varies depending on the temperature. It is preferred that the period of time is usually from 0.5 to 3 hours or so from the viewpoint of homogenizing the texture of the aqueous gel constituting the blood vessel model. After the temperature of the blood vessel model is controlled, the blood vessel model may be allowed to stand to cool to room temperature.

The blood vessel model of the present invention is usually produced so as to have an outer diameter and an inner diameter similar to those of the blood vessel of the human body. Therefore, it is preferred that the outer diameter of the blood vessel model of the present invention is usually controlled to 2 to 5 mm or so, and that the inner diameter of the blood vessel model is usually controlled to 1 to 3 mm or so.

The blood vessel model of the present invention can be used as a blood vessel model as it is, and may be cut so as to have a desired length as occasion demands. The blood vessel model of the present invention also can be produced by molding a blood vessel model having a predetermined outer diameter and a predetermined inner diameter which are larger than those of a blood vessel of the human body, and drawing the blood vessel model to have a desired outer diameter and a desired inner diameter.

The internal of the blood vessel model of the present invention may be hollow. Alternatively, the internal can be filled with a liquid similar to blood. For example, when the internal of the blood vessel model is filled with a liquid having a color similar to that of blood, the blood vessel model can be used as a blood vessel model filled with the liquid similar to the blood.

In the blood vessel model of the present invention, an aneurysm-shaped blood vessel model which imitates an aneurysm having a diameter of several cm, for example, 3 to 6 cm or so may be formed between one blood vessel model and another blood vessel model.

The aneurysm-shaped blood vessel model can be produced, for example, by applying the above-mentioned mixed solution to the surface of a balloon-shaped spherical body having a predetermined diameter, which is expanded by blowing air into the spherical body, followed by freezing and thawing in accordance with the method for producing a blood vessel model of the present invention. The spherical body in the aneurysm-shaped blood vessel model can be removed by shrinkage. When the shrunk spherical body is removed from the aneurysm-shaped blood vessel model, a hole can be formed in this blood vessel model. This hole can be used as a passage of blood by connecting this hole with the inner hole of a straight tubular blood vessel model.

The blood vessel model in which an aneurysm-shaped blood vessel model is connected with a straight tubular blood vessel model can be produced, for example, by bonding the aneurysm-shaped blood vessel model with the straight tubular blood vessel model to connect the inside space of both models with each other, and applying a mixed solution to the connected portion of both models, followed by freezing and thawing in accordance with the method for producing a blood vessel model of the present invention. When a blood vessel model is produced in the above manner, the leakage of a liquid being filled in the blood vessel can be avoided at the connected portion of the aneurysm-shaped blood vessel model and the straight tubular blood vessel model.

The aneurysm-shaped blood vessel model thus obtained can be suitably used, for example, as a blood vessel model for practicing insertion of a stent graft into a large aneurysm, a blood vessel model for practicing surgery including resecting a large aneurysm, and then implanting an artificial blood vessel in place of the large aneurysm, and the like. Its one embodiment is described below with reference to a drawing.

FIG. 2 is a schematic drawing for the explanation of manipulation training carried out by inserting a stent graft into the blood vessel model having a large aneurysm of the present invention.

FIG. 2($a$) shows a blood vessel model having a large aneurysm 2 formed in an aorta 1. When the large aneurysm 2 existing in the human body is allowed to stand as it is, the large aneurysm 2 may rupture, resulting in death. Therefore, as shown in FIG. 2($b$), a catheter 4 including a stent graft 3 is inserted to the position where the large aneurysm 2 exists, and the stent graft 3 is taken out from the catheter 4 at the position where the large aneurysm 2 exists. Thereafter, the stent graft 3 is spread in the aorta 1 so as to cover the large aneurysm 2. Since the large aneurysm 2 is covered with the stent graft 3 by the above operation, blood does not flow into the large aneurysm 2. Therefore, as shown in FIG. 2($c$), the large aneurysm 2 shrinks, and thus rupture of the large aneurysm 2 can be prevented.

The practice of treatment of the large aneurysm by using such a stent graft cannot be applied to the living body. Therefore, it has recently been desired to develop a blood vessel model for practicing insertion of a stent graft into the aorta. This desire can be satisfied with the blood vessel model of the present invention.

The blood vessel model of the present invention can be used as a blood vessel model for practicing resection of a blood vessel portion having a large aneurysm and implantation of an artificial blood vessel in place of the resected blood vessel portion. In this case, it is possible to use a blood vessel model having a large aneurysm 2 in an aorta 1 as shown in FIG. 2($a$). In this case, for example, bleeding is stopped by clipping the blood vessel before and after the large aneurysm 2 of a blood vessel model with forceps. After resecting the blood vessel model having the large aneurysm 2 between both forceps, a blood vessel model having a healthy blood vessel shape is applied to the thus resected position, followed by ligation of both end portions of this blood vessel model with the blood vessel model in which the large aneurysm 2 is resected. Thus, treatment practice is completed.

Accordingly, it is possible to practice resecting a blood vessel having an aneurysm in an aorta and practice ligating both end portions of the thus resected blood vessel and a healthy blood vessel by using the blood vessel model of the present invention as a blood vessel model for practicing manipulation in which a blood vessel portion having a large aneurysm is resected and an artificial blood vessel is implanted in place of the resected blood vessel portion.

In the present invention, as described above, the silica particles and the polyvinyl alcohol are used in combination as raw materials. Therefore, it is possible to efficiently obtain a blood vessel model which has hydrophilicity like a blood vessel of the human body and a surface free from stickiness, and which also has flexibility (resilience), incision feeling like a blood vessel of the human body and satisfactory mechanical strength, by performing freezing and thawing of the mixed solution only one time without the repeating of an operation for freezing and thawing of the mixed solution plural times. Incidentally, the operation for freezing and thawing may be repeated plural times as occasion demands.

As described above, the blood vessel model of the present invention has hydrophilicity like a blood vessel of the human body and a surface free from stickiness, and also has flexibility (resilience) and incision feeling like a blood vessel of the human body. Also, the blood vessel model containing the cross-linked gel and the silica particles of the present invention has a surface free from stickiness, and also has moderate hydrophilicity, flexibility (resilience) and a suitable tensile strength.

Accordingly, the blood vessel model of the present invention can be suitably used, for example, as a blood vessel model for practicing insertion of a stent graft into a blood vessel having an aneurysm, and a blood vessel model for practicing resection or ligation surgery of a blood vessel.

EXAMPLES

Next, the present invention will be more specifically described by way of examples, but the present invention is not limited only to those examples.

Example 1

A polyvinyl alcohol having an average polymerization degree of 1700 and a saponification degree of about 98 to about 99% by mole [manufactured by KURARAY CO., LTD. under the trade name of KURARAY POVAL PVA-117] was dissolved in water to prepare an aqueous polyvinyl alcohol solution in which the concentration of polyvinyl alcohol was 10% by weight. After stirring the obtained aqueous polyvinyl alcohol solution for 15 minutes while warming to 80° C., the solution was allowed to stand to cool to room temperature. This aqueous polyvinyl alcohol solution in an amount of 500 mL was charged in a 1 L (liter) beaker.

Next, 15 mL of colloidal silica [manufactured by Nissan Chemical Industries, Ltd. under the trade name of SNOWTEX XP, particle diameter of silica: about 5 nm, content of silica: 5% by weight] was added to the beaker at room temperature, followed by stirring so as to form uniform contents in the beaker, to give a mixed solution.

To the mixed solution in the beaker, 0.5 mL of a semitransparent acrylic poster color having a chestnut color similar to the color of a human blood vessel [manufactured by Delta Corporation under the trade name of DeltaCeramcoat] was added, followed by stirring so as to form uniform components.

A rubber plug made of a silicone rubber was inserted into the opening at one end of a straight tube made of an acrylic resin and having a outer diameter of 5 mm, an inner diameter of 4 mm and a length of 200 mm, and a core material made of an acrylic resin having a diameter of 2 mm and a length of 250 mm was inserted into the hole for inserting a core material provided at the central portion of the rubber plug. The opening at another end of this straight tube was faced upward, and the tinted mixed solution obtained in the above (liquid temperature: 20° C.) was poured into the gap between the straight tube and the core material up to the vicinity of the opening at another end of the straight tube so that no air bubbles infiltrated. Thereafter, a core material was penetrated into the hole for inserting the core material provided at the central portion of the rubber plug made of a silicone rubber, and the rubber plug was inserted into the opening of the straight tube.

Next, this straight tube was placed in a freezing chamber (temperature in the freezing chamber: −20° C.), cooled for 5 hours, taken out from the freezing chamber and then allowed to stand at room temperature to have room temperature.

Next, this straight tube was placed in a dryer, heated to 60° C., maintained at the same temperature for 10 minutes, taken out from the dryer, and then allowed to stand to cool.

The obtained blood vessel model was taken out from this straight tube. The core material was taken out from this blood vessel model, and then dried to give a blood vessel model similar to a blood vessel of the human body. An acrylic poster color having a red color similar to the color of human blood [manufactured by Delta Corporation under the trade name of DeltaCeramcoat] was filled into the obtained blood vessel model. The blood vessel model thus obtained is shown in FIG. 1. FIG. 1 is a photograph, which is substituted for a drawing, of the blood vessel model. As shown in FIG. 1, a liquid similar to blood (black area in the drawing) exists inside the obtained blood vessel model, and it can be seen that the blood vessel model has a form similar to a blood vessel of the human body.

Example 2

A blood vessel model was produced in the same manner as in Example 1, except that polyvinyl alcohol having an average polymerization degree of 1000 and a saponification degree of about 98 to about 99% by mole [manufactured by KURARAY CO., LTD. under the trade name of KURARAY POVAL PVA-110] was used as polyvinyl alcohol in Example 1.

Example 3

A blood vessel model was produced in the same manner as in Example 1, except that polyvinyl alcohol having an average polymerization degree of 2000 and a saponification degree of about 98 to about 99% by mole [manufactured by KURARAY CO., LTD. under the trade name of KURARAY POVAL PVA-120] was used as polyvinyl alcohol in Example 1.

Example 4

A blood vessel model was produced in the same manner as in Example 1, except that the amount of colloidal silica was changed to 1 mL in Example 1.

Example 5

A blood vessel model was produced in the same manner as in Example 1, except that the amount of the colloidal silica was changed to 80 mL in Example 1.

Comparative Example 1

A blood vessel model was produced in the same manner as in Example 1, except that the colloidal silica was not used in Example 1.

Comparative Example 2

A polyvinyl alcohol powder (average polymerization degree: 1700, saponification degree: 99.0% by mole) in an amount of 80 g was mixed with a polyvinyl alcohol powder (average polymerization degree: 1800, saponification degree: 86 to 90% by mole) in an amount of 20 g to obtain a polyvinyl alcohol mixture. The obtained polyvinyl alcohol mixture was dissolved in a mixed solvent of dimethyl sulfoxide and water [dimethyl sulfoxide/water (weight ratio): 80/20] while heating to 120° C. to prepare a polyvinyl alcohol solution having a water content of 80% by weight.

The same procedures as in Example 1 were carried out except that the polyvinyl alcohol solution obtained in the above was used in place of the mixed solution used in Example 1. The polyvinyl alcohol solution obtained in the above (liquid temperature: 45° C.) was poured into the gap between the straight tube and the core material up to the vicinity of the opening at another end of the straight tube so that no air bubbles infiltrated. Then, a core material was penetrated into the hole for inserting a core material provided at the central portion of a rubber plug made of a silicone rubber, and the rubber plug was inserted into the opening of the straight tube.

Next, this straight tube was placed in a freezing chamber (temperature in the freezing chamber: −20° C.), cooled for 6 hours, taken out from the freezing chamber, and then allowed to stand at room temperature, to have room temperature. The rubber plug at both ends of this straight tube was removed, and the core material was taken out from the straight tube. This straight tube was dipped in 200 mL of ethanol for 2 hours at room temperature, whereby dimethyl sulfoxide was substituted with ethanol to remove. After dipping the straight tube in water at 25° C., this straight tube was taken out from the water, and the obtained blood vessel model was taken out from the straight tube.

This blood vessel model was observed with naked eyes. As a result, it was confirmed that the blood vessel model was not sufficiently gelled, had scarcely resilience, and also had fluidity and stickiness on its surface. Therefore, this model was unsuitable for a blood vessel model.

Therefore, it can be seen that a blood vessel model cannot be obtained, since gelling of the obtained polyvinyl alcohol does not sufficiently proceed, even though polyvinyl alcohol having an average polymerization degree of 1700 and a saponification degree of 99.0% by mole is mixed with polyvinyl alcohol having an average polymerization degree of 1800 and a saponification degree of 86 to 90% by mole in a weight ratio of 80/20, and the mixture is dissolved in a mixed solvent of water and dimethyl sulfoxide and cooled to room temperature.

Comparative Example 3

The same procedures as in Comparative Example 1 were carried out except that the polyvinyl alcohol solution was poured into the straight tube made of an acrylic resin having a volume of 200 mL, that the temperature for cooling this resin container was changed from room temperature to −20° C., followed by freezing at this temperature for 24 hours, and that the temperature was returned to room temperature to thaw. As a result, a gel was obtained unlike Comparative Example 1. However, it was confirmed that the obtained gel had poor resilience and stickiness on its surface.

Comparative Example 4

A blood vessel model was produced by cutting a commercially available silicone rubber tube having a diameter of 2 mm into pieces each having a length of 20 cm.

Test Example 1

As physical properties, appearance, water wettability (hydrophilicity), sticky feeling, resilience and incision feeling of blood vessel models obtained in each Example and each Comparative Example were examined in accordance with the following methods. The results are shown in Table 1.

(1) Appearance

Ten students and teachers who majored in surgery in a graduate school of medicine of a university were asked to observe the appearance of each blood vessel model, and the appearance was evaluated in accordance with the following evaluation criteria. Incidentally, acceptable standard is that nobody rates "D".

[Evaluation Criteria]
A: hardly distinguishable from a blood vessel of living body
B: very similar to a blood vessel of living body
C: sufficiently similar to a blood vessel of living body
D: unsimilar to a blood vessel of living body (2) Water Wettability (Hydrophilicity)

A water drop was dropped on the blood vessel model, and ten students and teachers who majored in surgery in a graduate school of medicine of a university were asked to observe the surface of the blood vessel model with naked eyes. The water wettability was evaluated in accordance with the following evaluation criteria. Incidentally, acceptable standard is that nobody rates "D".

[Evaluation Criteria]
A: hardly distinguishable from a blood vessel of living body
B: very similar to a blood vessel of living body
C: sufficiently similar to a blood vessel of living body
D: unsimilar to a blood vessel of living body (3) Sticky Feeling Ten students and teachers who majored in surgery in a graduate school of medicine of a university were asked to examine sticky feeling of the blood vessel model by finger touching, and sticky feeling was evaluated in accordance with the following evaluation criteria. Incidentally, acceptable standard is that nobody rates "D".

[Evaluation Criteria]
A: hardly distinguishable from a blood vessel of living body
B: very similar to a blood vessel of living body
C: sufficiently similar to a blood vessel of living body
D: unsimilar to a blood vessel of living body (4) Resilience Ten students and teachers who majored in surgery in a graduate school of medicine of a university were asked to examine resilience of the blood vessel model by finger touching, and the resilience was evaluated in accordance with the following evaluation criteria. Incidentally, acceptable standard is that nobody rates "D".

[Evaluation Criteria]
A: hardly distinguishable from a blood vessel of living body
B: very similar to a blood vessel of living body
C: sufficiently similar to a blood vessel of living body
D: unsimilar to a blood vessel of living body (5) Incision Feeling Ten students and teachers who majored in surgery in a graduate school of medicine of a university were asked to examine incision feeling of each blood vessel model by actually operating with a surgical scalpel [surgical change-edge surgical knife No. 10 made of stainless steel, manufactured by FEATHER Safety Razor Co., Ltd.], and incision feeling was evaluated in accordance with the following evaluation criteria. Incidentally, acceptable standard is that nobody rates "D".

[Evaluation Criteria]
A: hardly distinguishable from a blood vessel of living body
B: very similar to a blood vessel of living body
C: sufficiently similar to blood vessel of living body
D: unsimilar to blood a vessel of living body In Comparative Example 1, since a gel could not be produced, physical properties of the blood vessel model could not be determined.

TABLE 1

| Example and Comparative | Appearance | | | | Water wettability | | | | Sticky feeling | | | | Resilience | | | | Incision feeling | | | |
|---|---|---|---|---|---|---|---|---|---|---|---|---|---|---|---|---|---|---|---|---|
| Example No. | A | B | C | D | A | B | C | D | A | B | C | D | A | B | C | D | A | B | C | D |
| 1 | 9 | 1 | 0 | 0 | 9 | 1 | 0 | 0 | 8 | 2 | 0 | 0 | 9 | 1 | 0 | 0 | 9 | 1 | 0 | 0 |
| 2 | 7 | 2 | 1 | 0 | 9 | 1 | 0 | 0 | 7 | 2 | 1 | 0 | 8 | 2 | 0 | 0 | 9 | 1 | 0 | 0 |
| 3 | 7 | 1 | 2 | 0 | 9 | 1 | 0 | 0 | 7 | 3 | 0 | 0 | 8 | 1 | 1 | 0 | 8 | 1 | 1 | 0 |
| 4 | 7 | 2 | 1 | 0 | 8 | 2 | 0 | 0 | 8 | 2 | 0 | 0 | 8 | 2 | 0 | 0 | 8 | 2 | 0 | 0 |
| 5 | 8 | 1 | 1 | 0 | 8 | 2 | 0 | 0 | 7 | 2 | 1 | 0 | 7 | 3 | 0 | 0 | 7 | 2 | 1 | 0 |
| Comp. Ex. | | | | | | | | | | | | | | | | | | | | |
| 1 | 6 | 2 | 2 | 0 | 5 | 4 | 1 | 0 | 2 | 4 | 3 | 1 | 1 | 1 | 4 | 4 | 0 | 1 | 5 | 4 |
| 2 | — | — | — | — | — | — | — | — | — | — | — | — | — | — | — | — | — | — | — | — |
| 3 | 7 | 3 | 0 | 0 | 5 | 3 | 1 | 1 | 0 | 0 | 2 | 8 | 0 | 0 | 3 | 7 | 0 | 0 | 4 | 6 |
| 4 | 7 | 3 | 0 | 0 | 0 | 0 | 1 | 9 | 2 | 3 | 3 | 2 | 1 | 2 | 3 | 4 | 0 | 0 | 2 | 8 |

It can be seen from the results shown in Table 1 that the blood vessel model obtained in each Example has appearance and water wettability similar to a blood vessel of the living body and a surface free from stickiness, and also has resilience and incision feeling like a blood vessel of the human body, since the blood vessel model containing polyvinyl alcohol and silica particles is used.

Example 6

Two blood vessel models each having an outer diameter of 4 mm, an inner diameter of 2 mm and a length of 200 mm were produced in the same manner as in Example 1. The two blood vessel models were intersected with each other, and a hole having a diameter of about 2 mm was formed at the intersected portion in each blood vessel model. The two blood vessel models were connected with each other so that the inside of each blood vessel model was communicated with each other, and the mixed solution obtained in Example 1 was applied to the intersected portion so as to seal the intersected portion.

In the obtained blood vessel model integrated by intersecting the two blood vessel models, an opening having a diameter of about 2 mm was formed on the side surface of one of the blood vessel models.

Apart from this blood vessel model, a large aneurysm-shaped blood vessel model which imitated an aneurysm was produced by using the mixed solution obtained in Example 1. More specifically, this aneurysm-shaped blood vessel model was produced by applying the mixed solution obtained in Example 1 to the surface of a rubber balloon expanded by blowing air to have a diameter of about 8 mm; carrying out freezing and thawing in the same manner as in Example 1 to produce an aneurysm-shaped blood vessel model; pricking the blood vessel model with a needle thereby causing the balloon to rupture inside the blood vessel model; removing the needle; and then taking out the balloon from the formed opening having a diameter of about 2 mm.

The opening of the aneurysm-shaped blood vessel model obtained in the above was intersected with the opening positioned at the side surface of the blood vessel model produced by intersecting and integrating the two blood vessel models obtained in the above, and the inside of each blood vessel model was communicated with each other. The mixed solution obtained in Example 1 was applied to the intersected portion so as to seal the intersected portion. Thereafter, freezing and thawing of the model was carried out in the same manner as in Example 1, to give a blood vessel model having an aneurysm-shaped blood vessel. An acrylic poster color having a red color similar to the color of human blood [manufactured by Delta Corporation under the trade name of Delta-Ceramcoat] was filled into the obtained blood vessel model. The obtained blood vessel model is shown in FIG. 3.

FIG. 3 is a photograph, which is substituted for a drawing, of the blood vessel model obtained in the above. As shown in FIG. 3, it can be seen that a liquid similar to blood (black area in the drawing) exists inside the obtained blood vessel model, and that a lump similar to an aneurysm exists on the left side of the intersected portion of the two blood vessel models in the blood vessel model which extends in a lateral direction facing the drawing.

Next, the surgeon was asked to observe the obtained blood vessel model. As a result, as to this blood vessel model, there could be obtained high evaluation, such that the blood vessel model could be sufficiently expected to be used as a blood vessel model for practicing surgery for implanting an artificial blood vessel in an aneurysm, a blood vessel model for practicing insertion of a stent graft into an aneurysm, and the like.

From the above facts, it can be seen that the blood vessel model of the present invention can be suitably used, for example, as a blood vessel model for practicing insertion of a stent graft into an aneurysm, a blood vessel model for practicing resection or ligation surgery of a blood vessel, and the like.

Example 7

A 500 mL volume beaker was charged with 80 mL of dimethyl sulfoxide and 20 mL of water, and they were sufficiently mixed with each other, to give a mixed solvent. To 100 mL of the mixed solvent in the above beaker, 20 mL of colloidal silica [manufactured by Nissan Chemical Industries, Ltd. under the trade name of SNOWTEX XP, particle diameter of silica: about 5 nm, content of silica: 5% by weight] was added, followed by stirring so that the contents in the beaker became uniform.

Next, polyvinyl alcohol having an average polymerization degree of 1700 and a saponification degree of 98 to 99% by mole or so [manufactured by KURARAY CO., LTD. under the trade name of KURARAY POVAL PVA-117] was added to the beaker to have a concentration of 10% by weight. The mixture was stirred for 15 minutes while heating to 80° C., to give a mixed solution.

To the obtained mixed solution, 0.15 mL of a semitransparent acrylic poster color having a chestnut color similar to the color of a human blood vessel [manufactured by Delta Corporation under the trade name of DeltaCeramcoat] was added, followed by stirring, to form homogeneous components.

A rubber plug made of a silicone rubber was inserted to the opening at one end of a straight tube made of an acrylic resin having an outer diameter of 5 mm, an inner diameter of 4 mm and a length of 200 mm, and a core material made of an acrylic resin having a diameter of 2 mm and a length of 250 mm was inserted to the hole for inserting a core material formed at the central portion of the rubber plug. The opening positioned at another end of this straight tube was facing upward, and the tinted mixed solution obtained in the above (liquid temperature: 45° C.) was poured into the gap between the straight tube and the core material up to the vicinity of the opening at another end of the straight tube so that no air bubbles infiltrated. Thereafter, a core material was penetrated to the hole for inserting a core material formed at the central portion of the rubber plug made of a silicone rubber, and the rubber plug was inserted to the opening of the straight tube.

Next, this straight tube was placed in a freezing chamber (temperature in the freezing chamber: −20° C.), cooled for 6 hours, taken out from the freezing chamber and then allowed to stand at room temperature to have room temperature.

The obtained blood vessel model was taken out from this straight tube, and the core material was taken out from this blood vessel model. This blood vessel model was dipped in water in a container charged with 5 L of water at 25° C. The container was allowed to stand for 24 hours while supplying water to this container at a flow rate of 200 mL/min, and then the blood vessel model was taken out from the container.

An acrylic poster color having a red color similar to the color of human blood [manufactured by Delta Corporation under the trade name of DeltaCeramcoat] was filled into a part of the inner space of this blood vessel model. The blood vessel model thus obtained is shown in FIG. 4. FIG. 4 is a photograph, which is substituted for a drawing, of the blood vessel model obtained in the above. As shown in FIG. 4, it can be seen that a liquid similar to blood (black area in the drawing) exists inside the obtained blood vessel model, and that the blood vessel model has a form similar to a blood vessel of the human body.

Example 8

A blood vessel model was produced in the same manner as in Example 7, except that polyvinyl alcohol having an average polymerization degree of 1000 and a saponification degree of about 98 to about 99% by mole [manufactured by KURARAY CO., LTD under the trade name of KURARAY POVAL PVA-110] was used as polyvinyl alcohol in Example 7.

Example 9

A blood vessel model was produced in the same manner as in Example 7, except that polyvinyl alcohol having an average polymerization degree of 2000 and a saponification degree of about 98 to about 99% by mole [manufactured by KURARAY CO., LTD. under the trade name of KURARAY POVAL PVA-120] was used as polyvinyl alcohol in Example 7.

Example 10

A blood vessel model was produced in the same manner as in Example 7, except that the amount of colloidal silica was changed to 5 mL in Example 7.

Example 11

A blood vessel model was produced in the same manner as in Example 7, except that the amount of colloidal silica was changed to 50 mL in Example 7.

Example 12

A blood vessel model was produced in the same manner as in Example 7, except that 75 mL of dimethyl sulfoxide and 25 mL of water were used in place of 80 mL of dimethyl sulfoxide and 20 mL of water in Example 7.

Example 13

A blood vessel model was produced in the same manner as in Example 7, except that 85 mL of dimethyl sulfoxide and 15 mL of water were used in place of 80 mL of dimethyl sulfoxide and 20 mL of water in Example 7.

Comparative Example 5

A blood vessel model was produced in the same manner as in Example 7, except that the colloidal silica was not used in Example 7.

Comparative Example 6

A polyvinyl alcohol powder (average polymerization degree: 1700, saponification degree: 99.0% by mole) in an amount of 80 g was mixed with a polyvinyl alcohol powder (average polymerization degree: 1800, saponification degree: 86 to 90% by mole) in an amount of 20 g to obtain a polyvinyl alcohol mixture. The obtained polyvinyl alcohol mixture was dissolved in a mixed solvent of dimethyl sulfoxide and water [dimethyl sulfoxide/water (weight ratio): 80/20] while heating to 120° C. to prepare a polyvinyl alcohol solution having a water content of 80% by weight.

The same procedures as in Example 7 were carried out except that the polyvinyl alcohol solution obtained in the above was used in place of the mixed solution used in Example 7, and the polyvinyl alcohol solution (liquid temperature: 45° C.) was poured into the gap between the straight tube and the core material up to the vicinity of an opening at another end of the straight tube so that no air bubbles infiltrated. Then, a core material was penetrated to the hole for inserting a core material formed at the central portion of a rubber plug made of a silicone rubber, and the rubber plug was inserted to the opening of the straight tube.

Next, this straight tube was placed in a freezing chamber (temperature in the freezing chamber: −20° C.), cooled for 6 hours, taken out from the freezing chamber and then allowed to stand at room temperature to have room temperature. The rubber plug at both ends of this straight tube was removed and the core material was taken out from the straight tube. This straight tube was dipped in 200 mL of ethanol for 2 hours at room temperature, and dimethyl sulfoxide was substituted with ethanol to remove. The straight tube was dipped in water at 25° C., and this straight tube was taken out from the water. The obtained blood vessel model was taken out from the straight tube.

This blood vessel model was observed with naked eyes. As a result, it was confirmed that the blood vessel model was not sufficiently gelled and had scarcely resilience, and also had fluidity and stickiness on its surface. Therefore, this model could not be used as a blood vessel model.

Accordingly, it can be seen that a blood vessel model cannot be obtained, since gelling of the obtained polyvinyl alcohol does not sufficiently proceed, even though polyvinyl alcohol having an average polymerization degree of 1700 and a saponification degree of 99.0% by mole is mixed with polyvinyl alcohol having an average polymerization degree of 1800 and a saponification degree of 86 to 90% by mole in a weight ratio of 80/20, and the mixture is dissolved in a mixed solvent of water and dimethyl sulfoxide and cooled to room temperature.

Comparative Example 7

The same procedures as in Comparative Example 5 were carried out, except that a polyvinyl alcohol solution was poured into a straight tube made of an acrylic resin having a volume of 200 mL, and then the temperature for cooling this resin container was changed from room temperature to −20° C., that freezing was carried out at this temperature for 24 hours, and that the temperature was returning to room temperature to thaw. As a result, a gel-like blood vessel model was obtained, unlike Comparative Example 5. However, it was confirmed that the obtained blood vessel model has poor flexibility (resilience), and has stickiness on its surface.

Test Example 2

As physical properties, transparency, water wettability (hydrophilicity), flexibility (resilience), sticky feeling and tensile strength of the blood vessel models obtained in each Example and each Comparative Example were examined in accordance with the following methods. The results are shown in Table 2.

(1) Transparency

Each blood vessel model was observed with naked eyes, and transparency was evaluated in accordance with the following evaluation criteria.
[Evaluation Criteria]
A: excellent transparency
B: satisfactory transparency
C: slightly poor transparency
D: poor transparency (2) Water Wettability (Hydrophilicity)

A water drop was dropped on each blood vessel model, and the surface of the blood vessel model was observed with naked eyes. The water wettability was evaluated in accordance with the following evaluation criteria.
[Evaluation Criteria]
A: water wettability suitable for a blood vessel model for surgical training
B: water wettability slightly suitable for a blood vessel model for surgical training
C: water wettability less suitable for a blood vessel model for surgical training
D: unsuitable for a blood vessel model for surgical training (3) Flexibility (Resilience)

Flexibility (resilience) of each blood vessel model was examined by finger touching, and evaluated in accordance with the following evaluation criteria.
[Evaluation Criteria]
A: flexibility (resilience) suitable for a blood vessel model for surgical training
B: flexibility (resilience) slightly suitable for a blood vessel model for surgical training
C: flexibility (resilience) less suitable for a blood vessel model for surgical training
D: unsuitable for a blood vessel model for surgical training (4) Sticky Feeling Sticky feeling of each blood vessel model was examined by finger touching, and evaluated in accordance with the following evaluation criteria.
[Evaluation Criteria]
A: scarcely sticky
B: a little sticky but no hindrance
C: clearly sticky
D: considerably sticky (5) Tensile Strength Both ends of each blood vessel model were pinched with a thumb and the first finger of both hands, and then drawn. The tensile strength was evaluated in accordance with the following evaluation criteria.
[Evaluation Criteria]
A: excellent tensile strength
B: satisfactory tensile strength
C: slightly poor tensile strength
D: poor tensile strength In Comparative Example 6, since a gel could not be produced, physical properties of the blood vessel model could not be examined.

TABLE 2

| Ex. and Comp. Ex. No. | Physical properties of blood vessel model ||||| 
|---|---|---|---|---|---|
| | Transparency | Water wettability | Flexibility | Sticky feeling | Tensile strength |
| 7 | A | A | A | A | A |
| 8 | A | A | A | A | B |
| 9 | A | B | B | A | A |
| 10 | B | B | A | B | A |
| 11 | A | B | A | A | A |
| 12 | A | A | A | A | A |
| 13 | B | B | B | B | B |
| Comp. Ex. | | | | | |
| 5 | B | B | C | C | D |
| 6 | — | — | — | — | — |
| 7 | C | C | D | D | D |

From the results shown in Table 2, it can be seen that the blood vessel model obtained in each Example is excellent in transparency and has moderate hydrophilicity and flexibility, and has a surface free from stickiness and large tensile strength.

Example 14

Two blood vessel models each having an outer diameter of 4 mm, an inner diameter of 2 mm and a length of 200 mm were produced in the same manner as in Example 7. The two blood vessel models were intersected with each other, and a hole having a diameter of about 2 mm was formed at the intersected portion in each blood vessel model. The two blood vessel models were connected with each other so that the inside of each blood vessel model was communicated with each other, and the mixed solution obtained in Example 7 was applied to the intersected portion so as to seal the intersected portion.

In the obtained blood vessel model integrated by intersecting the two blood vessel models, an opening having a diameter of about 2 mm was formed on the side surface of one of the blood vessel models.

Apart from this blood vessel model, a large aneurysm-shaped blood vessel model which imitated an aneurysm was produced by using the mixed solution obtained in Example 7. More specifically, this aneurysm-shaped blood vessel model was produced by applying the mixed solution obtained in Example 7 to the surface of a rubber balloon expanded by blowing air to have a diameter of about 8 mm; carrying out freezing and thawing in the same manner as in Example 7 to produce an aneurysm-shaped blood vessel model; pricking the blood vessel model with a needle, and thereby causing the balloon to rupture inside the blood vessel model; removing the needle; and then taking out the balloon from the formed opening having a diameter of about 2 mm.

The opening of the aneurysm-shaped blood vessel model obtained in the above was intersected with the opening positioned at the side surface of the blood vessel model produced by intersecting and integrating two blood vessel models obtained in the above, and the inside of each blood vessel model was communicated with each other. The mixed solution obtained in Example 7 was applied to the intersected portion so as to seal the intersected portion. Thereafter, freezing and thawing of the model was carried out in the same manner as in Example 7, to give a blood vessel model having an aneurysm-shaped blood vessel. An acrylic poster color having a red color similar to the color of human blood [manufactured by Delta Corporation under the trade name of Delta-Ceramcoat] was filled into the obtained blood vessel model. The obtained blood vessel model is shown in FIG. 5.

FIG. 5 is a photograph, which is substituted for a drawing, of the blood vessel model obtained in the above. As shown in FIG. 5, it can be seen that a liquid similar to blood (black area in the drawing) exists inside the obtained blood vessel model, and that a lump similar to an aneurysm exists on the left side of the intersected portion of the two blood vessel models in the blood vessel model which extends in a lateral direction facing the drawing.

From the above facts, it can be seen that the blood vessel model of the present invention can be suitably used, for example, as a blood vessel model for practicing insertion of a stent graft into an aneurysm, a blood vessel model for practicing resection or ligation surgery of a blood vessel, and the like.

Reference Signs List

1: Aorta
2: Large aneurysm
3 Stent graft
4: Catheter

The invention claimed is:

1. A blood vessel model which imitates a human blood vessel, comprising an aqueous gel made from polyvinyl alcohol (A) and silica particles (B), wherein said polyvinyl alcohol (A) consists essentially of a polyvinyl alcohol having an average polymerization degree of 300 to 3500 and a saponification degree of 90% by mole or more, and the amount of silica particles (B) is from 0.01 to 50 parts by weight based on 100 parts by weight of the polyvinyl alcohol.

2. The blood vessel model according to claim 1, wherein colloidal silica is used as the silica particles.

3. The blood vessel model according to claim 1, wherein the blood vessel model is produced by freezing a mixed solution comprising the polyvinyl alcohol, the silica particles and water at a temperature of $-10°$ C. or lower, and thereafter thawing.

4. The blood vessel model according to claim 1, wherein the aqueous gel is a cross-linked gel.

5. The blood vessel model according to claim 4, wherein the cross-linked gel is a cross-linked gel being cross-linked with dimethyl sulfoxide.

6. The blood vessel model according to claim 5, wherein the blood vessel model is produced by cooling a mixed solution comprising polyvinyl alcohol, silica particles, dimethyl sulfoxide and water to a temperature of $-10°$ C. or lower, and thereafter thawing.

7. The blood vessel model according to claim 1, wherein the aqueous gel comprises a polysaccharide.

8. The blood vessel model according to claim 1, wherein the aqueous gel comprises a colorant.

\* \* \* \* \*